United States Patent
Kraas et al.

(10) Patent No.: US 6,749,559 B1
(45) Date of Patent: *Jun. 15, 2004

(54) ENDOSCOPE

(75) Inventors: Mathias Kraas, Haseldorf (DE); Andreas Mückner, Berlin (DE); Timo Wenzel, Hamburg (DE)

(73) Assignee: Olympus Winter & Ibe GmbH, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/576,270

(22) Filed: May 22, 2000

(30) Foreign Application Priority Data

May 27, 1999 (DE) .......................... 199 24 361

(51) Int. Cl.[7] ................................ A61B 1/00
(52) U.S. Cl. .................... 600/130; 600/101; 600/153
(58) Field of Search .................... 600/101–183

(56) References Cited

U.S. PATENT DOCUMENTS

| | | | |
|---|---|---|---|
| 4,633,304 A | * | 12/1986 | Nagasaki .................... 600/109 |
| 4,858,001 A | | 8/1989 | Milbank et al. |
| 4,884,133 A | | 11/1989 | Kanno et al. |
| 5,200,838 A | * | 4/1993 | Nudelman et al. .......... 600/108 |
| 5,235,965 A | | 8/1993 | Hiroya |
| 5,419,312 A | * | 5/1995 | Arenberg et al. ........... 600/108 |
| 5,603,687 A | * | 2/1997 | Hori et al. .................. 600/166 |
| 5,669,871 A | * | 9/1997 | Sakiyama .................... 600/117 |
| 5,779,625 A | * | 7/1998 | Suzuki et al. ............... 600/121 |
| 5,810,715 A | * | 9/1998 | Moriyama ................... 600/139 |
| 5,895,350 A | | 4/1999 | Hori |
| 5,899,851 A | | 5/1999 | Koninckx |
| 6,186,944 B1 | * | 2/2001 | Tsai ........................... 600/109 |

FOREIGN PATENT DOCUMENTS

| | | |
|---|---|---|
| JP | 60-182982 | 9/1985 |
| JP | 10-328131 | 12/1998 |

* cited by examiner

Primary Examiner—Beverly M. Flanagan
(74) Attorney, Agent, or Firm—Rankin, Hill, Porter & Clark LLP

(57) ABSTRACT

An endoscope having a tubular stem that, at its distal end, houses a camera and a distally pointing illumination device. The tubular stem defines an empty space extending from the camera in the proximal direction. The empty space receives a camera cable and is used to house implements useful during operation of the endoscope in a surgical procedure.

18 Claims, 1 Drawing Sheet

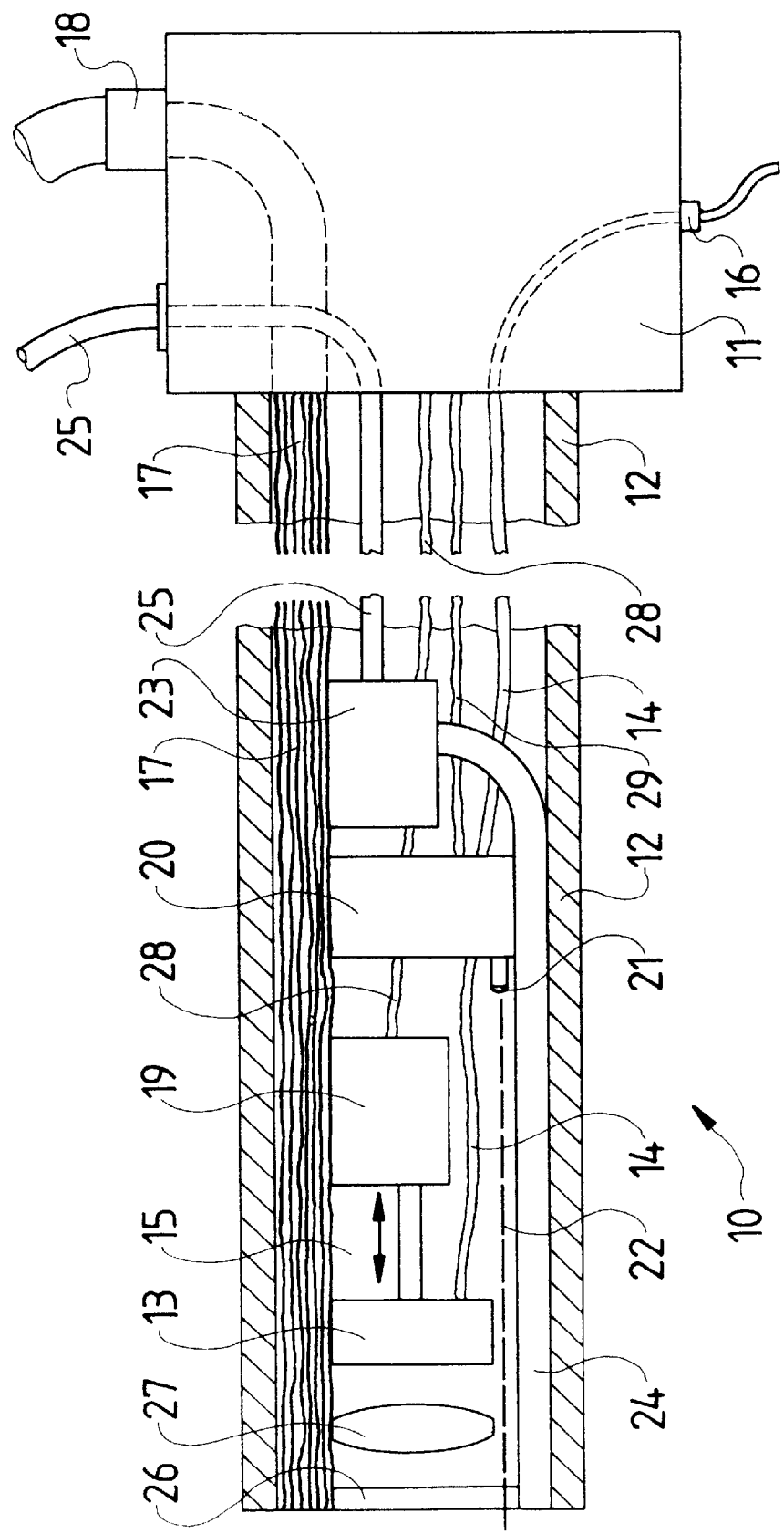

ENDOSCOPE

BACKGROUND OF THE INVENTION

The present invention is directed toward an endoscope having a tubular stem having a distal end and a proximal end, wherein the distal end receives a camera and a distally pointing illumination device, and wherein the tubular stem defines an empty space extending in the proximal direction away from the camera, the empty space receiving a camera cable.

An endoscope of the aforementioned type is known, for instance, from U.S. Pat. No. 4,858,001. This known endoscope, designed for dentistry, comprises a tubular stem fitted, at its distal end, with an electronic camera and with a distally pointing luminous source. The camera and the luminous source are fitted with conductors for power and data transmission. The conductors run inside the stem to a proximal main case where they terminate in outputs allowing connection to a power source or an image processor.

This design incurs the drawback that a comparatively large amount of free space goes unutilized in the vicinity of the conductors in the stem of such endoscopes.

SUMMARY OF THE INVENTION

Accordingly, the objective of the invention is that, starting with the state of the art, an endoscope shall be created which better utilizes space available in the stem of the endoscope.

According to the present invention, the available empty space in the tubular stem of the endoscope of the state of the art, which heretofore are filled only slightly by the conductors, shall be utilized to receive implements.

The endoscopes according to the invention especially are the just recently introduced video endoscopes. The term "implements" refers to and covers, in particular, devices facilitating handling the endoscopes and devices imparting an additional function to the endoscope.

Illustratively, in accordance with the present invention, the empty space inside the tubular stem may be utilized to receive a camera focusing drive. The video camera, for instance, is axially driven inside the stem into focus adjustment (zoom), or into auto-focus. The empty space may also receive a radial drive to adjust the viewing direction, whereby the image axis is kept constant for instance by means of corresponding stem rotations.

Furthermore, the empty space may be used to receive a drive means for a tool such as tongs or the like inside the endoscope. This drive means also may be a motor-actuated rotational or translational drive means permitting advancement/retraction of the implement, or otherwise actuating or manipulating the attachment.

Conceivably an implement turret selectively making available different tools also may be mounted in the empty space of the stem.

Obviously as well a laser means such as a pointer and illustratively being used as an operational laser in cutting or in diagnosis (PDD) also may be accommodated and used in the empty space.

Moreover, sensors may be configured in the empty space. Such sensors may, for example, be adapted to detect temperatures or pressures (for instance to monitor bladder pressure during endoscopic intervention), or other environmental of interest.

Lastly, a flushing pump may be received inside the stem's empty space. The flushing pump may be used to cool the camera or a laser. As another instance, a medication dispenser might also be configured in the empty space.

The above listing is not exhaustive, and the present invention is not limited thereto. Rather, it is considered clear that the empty space in the tubular endoscopic stem may be used in the manner of the invention for all commensurately-sized implements appropriate for endoscopes or endoscopic interventions.

Like conventional endoscopes, the endoscope of the invention includes, in addition to the distally mounted camera, a distally pointing illumination device to illuminate the region of surgery. The illumination device may be, for example, strands of light guides running in the endoscope from a proximal light source to the distal stem end. Such strands of light guides will, however, reduce the empty space available inside the stem to receive implements.

In a preferred embodiment of the invention, the illumination device at the distal end of the tubular stem is a diode that is connected to power by means of conductors extending through the stem. The conductors have substantially smaller diameters than the strands of light guides. Using such a diode substantially increases the empty space in the tubular endoscope stem receiving the implements.

The present invention offers many advantages. One substantial advantage is that endoscopes according to the present invention may implement further functions, as compared to conventional endoscopes, without diameter enlargement. As a result, handling of endoscopes according to the present invention is simplified because one endoscope can be used for a larger number of different functions than can conventional endoscopes. Accordingly, endoscopes incorporating the present invention are multi-functional, and there is a less frequent need for endoscope exchange in intervention.

BRIEF DESCRIPTION OF THE DRAWING

These and further features of the invention will be apparent with reference to the following description and drawing, wherein a partial cross section of an endoscope according to the present invention is illustrated.

DETAILED DESCRIPTION OF THE PREFERRED EMBODIMENT

The drawing FIGURE shows a diagrammatic partial section of an embodiment of the endoscope 10 of the invention.

With reference to the drawing FIGURE, an endoscope 10 according to the present invention is illustrated. The endoscope 10 comprises a proximal main case 11 to which is distally apposed a tubular stem 12. A camera 13 is mounted in the distal end zone of the tubular stem 12 and, by means of a lens 27, looks through a window 26 into a region of surgery (not shown).

The camera 13 is connected, via a cable 14, to an output 16 of the main case 11. The cable 14 runs or extends inside the empty space 15 of the stem 12. The cable 14 is indicated symbolically and denotes, where applicable, any conductors required for camera operation, such as for power and data transmission.

Accordingly the output 16 also may denote a larger number of outputs allowing, for instance, links to a remote image-processing unit (not shown) and to a power source.

The endoscope 10 furthermore comprises strands of light guides 17 running from a proximal light source (not shown) through a light input 18 and through the stem 12 until its distal end where, upon activation by the proximal light source, they will provide illumination to a region of surgery.

As already cited above, strands of light guides may be replaced, for instance, by a light-emitting diode (LED) at the distal end of the stem 12. This diode needs only to be connected by a cable to a proximal power source and as a result the available empty space 15 in the stem 12 will be enlarged.

The invention also allows using the empty space 15 of the stem 12 to house implements.

In this respect, a drive means 19 is mounted in the empty space 15. The drive means is used to displace the camera 13 in the direction of the arrow. The drive means 19 is powered by a cable 28 and illustratively can implement auto-focus and/or zoom operation, or also a displacement of the camera 13 in the direction of viewing.

The empty space 15 moreover contains a laser pointer 20 which, by means of a diode 21, emits a laser beam 22 into the region of surgery. The laser pointer 20 is powered through a cable 29, and may be used for diagnosis purposes.

A pump 23 may also be configured inside the empty space 15. The pump 23 communicates, via a flushing duct 24, with the region of surgery, and via a feed duct 25, with a reservoir (not shown) outside the endoscope.

It is considered apparent that the implements shown in the drawing FIGURE and described hereinbefore are merely exemplary, and that many other devices may alternatively and/or additionally be disposed in the empty space 15 of the stem 12. It is further considered apparent that the empty space may be utilized to receive only one implement rather then several implements simultaneously.

What is claimed is:

1. An endoscope (10) comprising:
    a main case (11);
    a tubular stem (12), said tubular stem having a proximal end, a distal end, a generally constant diameter and orientation between said proximal end and said distal end, and defining a longitudinal axis, said tubular stem proximal end being connected to said main case (11);
    a camera (13) and an objective (27) being disposed within said tubular stem near said distal end so as to look out of said tubular stem distal end;
    an illumination device disposed inside said tubular stem (12) near said distal end so as to look out of said distal end;
    wherein said tubular stem (12) defines an empty space (15) extending from said main case (11) to said camera (13), said empty space (15) receiving lines (14, 17) for connecting said camera (13) and said illumination device to said main case (11); and,
    wherein said empty space (14) receives, in addition to said connecting lines (14, 17), at least one implement (19, 20, 23).

2. The endoscope as claimed in claim 1, wherein illumination device is a diode.

3. The endoscope as claimed in claim 1, wherein said at least one implement is selected from the group consisting of: an adjustment drive means (19), an operational tool, a pump (23), and a sensor.

4. The endoscope as claimed in claim 1, wherein said at least one implement is a laser pointer (20).

5. The endoscope as claimed in claim 2, wherein said at least one implement is selected from the group consisting of: an adjustment drive means (19), an operational tool, a pump (23), and a sensor.

6. The endoscope as claimed in claim 2, wherein said at least one implement is a laser pointer (20).

7. An endoscope (10) comprising:
    a main case (11);
    a tubular stem (12), said tubular stem having a proximal end, a distal end, a generally constant diameter and orientation between said proximal end and said distal end, and defining a longitudinal axis, said tubular stem proximal end being connected to said main case (11), said longitudinal axis extending from said distal end to said proximal end;
    a camera (13) and an objective (27) being disposed within said tubular stem 12) near said tubular stem distal end so as to look out of said distal end;
    an illumination device disposed inside said tubular stem (12) near said distal end so as to look out of said distal end;
    wherein said tubular stem defines an empty space (15) extending from said main case (11) to said camera (13), said empty space being generally parallel to said longitudinal axis and receiving connecting lines (14, 17) for connecting said camera (13) and said illumination device to said main case (11), said empty space (15), in addition to receiving said connecting lines, receives at least one implement (19, 20, 23), and wherein said longitudinal axis extends past said camera and said implement.

8. The endoscope as claimed in claim 7, wherein the illumination device is a diode.

9. The endoscope as claimed in claim 7, wherein said at least one implement is selected from the group consisting of: an adjustment drive means (19), an operational tool, a pump (23), and a sensor.

10. The endoscope as claimed in claim 7, wherein said at least one implement is a laser pointer (20).

11. The endoscope as claimed in claim 8, wherein said at least one implement is selected from the group consisting of: an adjustment drive means (19), an operational tool, a pump (23), and a sensor.

12. The endoscope as claimed in claim 8, wherein said at least one implement is a laser pointer (20).

13. An endoscope (10) comprising:
    a main case (11);
    a tubular stem (12), said tubular stem being generally cylindrical and defining an outer surface of said endoscope, said tubular stem having a proximal end, a distal end, a generally constant diameter and orientation between said proximal end and said distal end, and defining a longitudinal axis, said tubular stem proximal end being connected to said main case (11) so as to define an interior space within said tubular stem, said longitudinal axis extending from said distal end to said proximal end;
    a camera (13) and an objective (27) disposed within said tubular stem (12) near said tubular stem distal end so as to look out of said tubular stem distal end;
    an illumination device disposed inside said tubular stem (12) near said tubular stem distal end so as to look out of said tubular stem distal end; and,
    wherein said tubular stem interior space includes an empty space extending from said main case to proximally adjacent said camera generally parallel to said longitudinal axis and receiving lines (14, 17) for con necting said camera (13) and said illumination device to said main casing (11), and wherein said empty space, in addition to receiving said connecting lines for said camera and said illumination device, receives at least one implement (19, 20, 23).

14. The endoscope as claimed in claim 13, wherein the distally pointing illumination device is a diode.

15. The endoscope as claimed in claim 13, wherein said at least one implement is selected from the group consisting of: an adjustment drive means (19), an operational tool, a pump (23), and a sensor.

16. The endoscope as claimed in claim 13, wherein said at least one implement is a laser pointer (20).

17. The endoscope as claimed in claim 14, wherein said at least one implement is selected from the group consisting of: an adjustment drive means (19), an operational tool, a pump (23), and a sensor.

18. The endoscope as claimed in claim 14, wherein said at least one implement is a laser pointer (20).

* * * * *